(12) United States Patent
Beckstein et al.

(10) Patent No.: US 9,937,300 B2
(45) Date of Patent: Apr. 10, 2018

(54) DUAL LUMEN CANNULA

(71) Applicant: Medone Surgical, Inc., Sarasota, FL (US)

(72) Inventors: Bruce Beckstein, Sarasota, FL (US); Segundo Rodriguez, Sarasota, FL (US); Christopher Riemann, Cincinnati, OH (US)

(73) Assignee: Medone Surgical, Inc., Sarasota, FL (US)

( * ) Notice: Subject to any disclaimer, the term of this patent is extended or adjusted under 35 U.S.C. 154(b) by 268 days.

(21) Appl. No.: 14/627,585

(22) Filed: Feb. 20, 2015

(65) Prior Publication Data
US 2015/0238707 A1    Aug. 27, 2015

Related U.S. Application Data

(60) Provisional application No. 61/942,842, filed on Feb. 21, 2014.

(51) Int. Cl.
*A61M 5/48*    (2006.01)
*A61M 5/32*    (2006.01)

(52) U.S. Cl.
CPC ............ *A61M 5/488* (2013.01); *A61M 5/329* (2013.01)

(58) Field of Classification Search
CPC .. A61M 5/488; A61M 5/329; A61M 25/0026; A61M 25/0071; A61M 2025/0004
See application file for complete search history.

(56) References Cited

U.S. PATENT DOCUMENTS

| | | | |
|---|---|---|---|
| 7,547,302 B2 * | 6/2009 | Porto | A61L 27/54 604/523 |
| 2004/0215130 A1 * | 10/2004 | Rioux | A61M 5/329 604/35 |
| 2006/0135963 A1 * | 6/2006 | Kick | A61B 17/221 606/108 |
| 2007/0255256 A1 * | 11/2007 | Fischer, Jr. | A61M 3/0283 604/528 |
| 2014/0100426 A1 * | 4/2014 | Barbour | A61M 5/3286 600/178 |
| 2015/0224284 A1 * | 8/2015 | Panotopoulos | A61M 25/0026 604/43 |

OTHER PUBLICATIONS

Medone Coaxial Dual Bore Cannula Information Sheet.

* cited by examiner

*Primary Examiner* — Lauren P Farrar
(74) *Attorney, Agent, or Firm* — Mintz Levin Cohn Ferris Glovsky and Popeo, P.C.; Peter F. Corless

(57) ABSTRACT

A dual lumen cannula is provided for conveying a fluid into an injection site through an inner lumen of the cannula. Fluid pressure is relieved from the injection site via a plurality of egress ports located along an outer lumen of the cannula.

18 Claims, 4 Drawing Sheets

DUAL LUMEN CANNULA

The present application claims priority of U.S. provisional application 61/942,842 filed Feb. 21, 2014, which is incorporated by reference herein in its entirety.

BACKGROUND (a) Technical Field

The present invention generally relates to a dual lumen cannula configured to relieve pressure at an injection site during injection of a fluid into a subject. In particular aspects, the present invention relates to a cannula having a first lumen configured to inject a fluid into a subject and a second lumen configured to divert fluid pressure away from the injection site via a plurality of openings in the cannula.

(b) Background Art

During some forms of surgery, a fluid may be injected into a subject that results in a buildup of fluid pressure at the injection site. For example, in eye surgery, a fluid-like balanced salt solution (BSS) may be injected into the eye before a second fluid is injected, such as a staining dye or perfluorocarbon liquid. Structurally, a human eye is semi-rigid in nature meaning that injection of a fluid into an eye will also cause an internal fluid pressure to form in the eye. Generally speaking, it is considered unsafe for an eye to have a high internal pressure for an extended period of time.

In addition to the potentially unsafe buildup of internal pressure at an injection site, an axial fluid "jet" effect may occur with some cannula designs. In particular, fluid injected through a cannula having an open end (i.e., through an opening at the very tip of the cannula) may cause an axial jet effect condition. For example, a jet effect may occur during eye surgery when a fluid is injected through an open-ended cannula close to the surface of the retina. The resulting jet effect can damage the retina by causing a perforation in the retina via the fluid stream and result in fluid being unintentionally injected under the retina.

Accordingly, there is a demand for the development of improved cannula designs that reduce and/or eliminate the presence of conditions that may cause damage to the injection site and surrounding areas during injection of a fluid.

The above information disclosed in this Background section is only for enhancement of understanding of the background of the invention and therefore it may contain information that does not form the prior art that is already known to a person of ordinary skill in the art.

SUMMARY

According to various embodiments, the present invention provides a cannula that includes an outer shaft that defines a first lumen that only partially extends through the outer shaft and terminates at an injection port located along the circumference of the outer shaft. The cannula also includes an inner shaft located within the first lumen that defines a second lumen configured to convey fluid through the inner shaft and the injection port of the outer shaft into an injection site. The outer shaft defines a plurality of egress ports located along the circumference of the outer shaft that are fluidically isolated from the injection port and configured to relieve fluid pressure from the injection site when fluid is conveyed from the second lumen into the injection site.

In some embodiments, the present invention provides a method in which a fluid is conveyed through a first lumen defined by an inner shaft of a cannula. The method also includes conveying the fluid through an injection port located along a circumference of an outer shaft of the cannula and into an injection site. The outer shaft of the cannula defines a second lumen configured to house the inner shaft. The method further includes conveying, in response to a fluid pressure at the injection site, fluid from the injection site through a plurality of egress ports located along the circumference of the outer shaft of the cannula that are fluidically isolated from the injection port.

In further embodiments, an apparatus is disclosed that includes means for conveying a fluid into an injection site. The apparatus also includes means for relieving fluid pressure from the injection site when the fluid is conveyed into the injection site.

BRIEF DESCRIPTION OF THE DRAWINGS

The above and other features of the present invention will now be described in detail with reference to certain exemplary embodiments thereof illustrated the accompanying drawings which are given herein by way of illustration only, and thus are not limitative of the present invention, and wherein.

Figure 1:
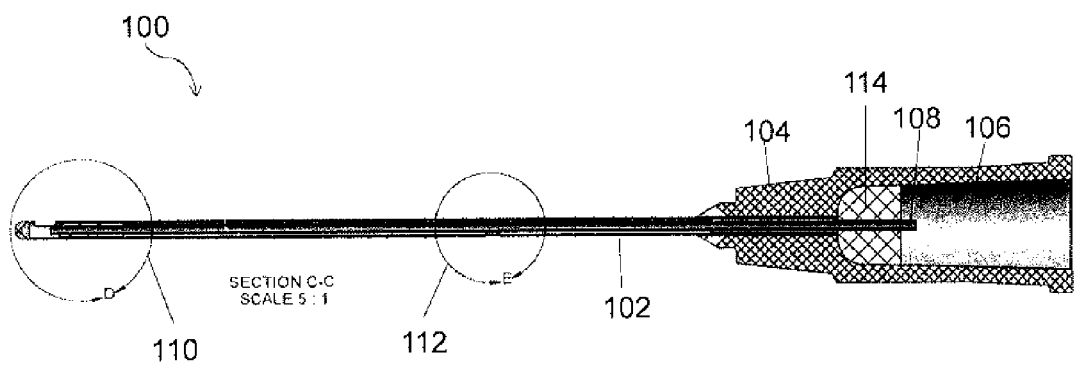
FIG. 1 is a cross-sectional view of a dual lumen cannula.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Advantageously, a dual lumen cannula is disclosed herein that releases, in a controlled manner, excess pressure generated when injecting a fluid into an injection site. For example, when used in eye surgery, the cannula disclosed herein allows excess pressure in an eye to be released in a controlled manner when additional fluid is injected into the eye.

Referring now to FIG. 1, a cross-sectional view of a cannula 100 is shown, according to various embodiments. As shown, cannula 100 is a dual lumen cannula having an inner shaft 108 that defines a first lumen and an outer shaft 102 that defines a second lumen. In some embodiments, cannula 100 may include a hub 104 or other connector configured to receive a syringe or similar device for injection of a fluid. A proximal end of inner shaft 108 may extend inside hub 104 or other connection fitting and into a cavity 106 configured to receive a corresponding connector of a syringe or other device that drives a fluid into cannula 100. For example, hub 104 may utilize a Luer type design or may be modified to reduce air pockets by use of a filler material 114 inside the front of hub 104. During operation, pressure is applied to a fluid to be injected (e.g., by a syringe). In response, the fluid is conveyed via inner shaft 108 through a middle portion 112 of cannula 100 and through a tip portion 110 into the injection site.

Figure 2:
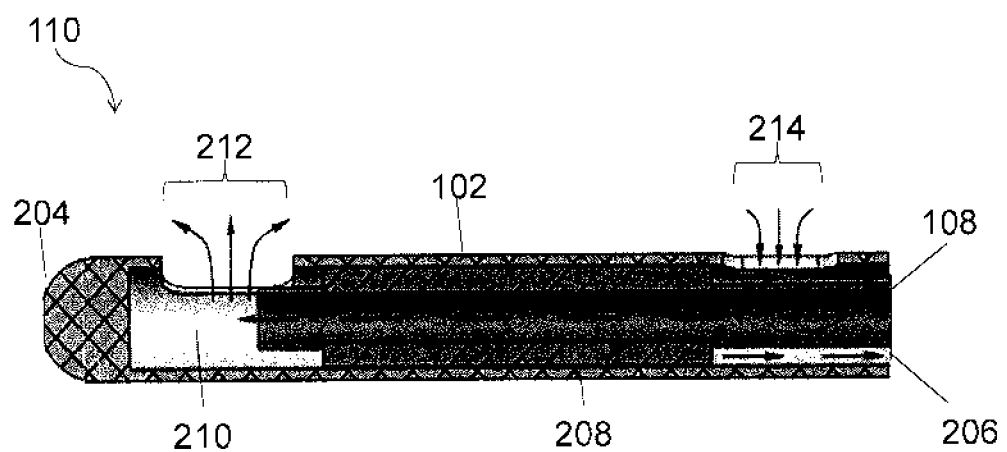
FIG. 2 is a cross-sectional view of a tip portion of the cannula of FIG. 1 shown in greater detail.

A cross-sectional view of tip portion 110 of cannula 100 is shown in greater detail in FIG. 2, according to various embodiments. As discussed above, cannula 100 has two coaxial lumens (i.e., as defined by shafts 102 and 108) that are mounted to a hub or similar fitting, to allow connection of the device to a syringe or other apparatus for injection of fluid. In some embodiments, outer shaft 102 includes a series of holes along its length, with the very tip 204 of outer shaft 102 being closed. In other words, lumen 210 defined by outer shaft 102 may partially extend through outer shaft 102 but does not extend through tip 204. Located near tip 204 is an injection port 212 that corresponds to the distal-most hole along outer shaft 102. Inner shaft 108 extends distally inside cannula 210 of outer shaft 102 with one end terminating at or near injection port 212. During operation of cannula 100, tip 204 is inserted into a subject and fluid is conveyed via inner shaft 108 through injection port 212 and into the injection site.

Dimensionally, cannula 100 may be made from any combination of tube sizes which allow adequate fluid ingress and egress capabilities. For eye surgery applications, for example, outer shaft 102 may be as large as approximately 20 gauge (9 mm) in diameter or as small as approximately 27 gauge (0.4 mm) in diameter. In particular, outer shaft 102 may have a diameter of 0.9 mm (20 gauge), 0.64 mm (23 gauge), 0.5 mm (25 gauge), and 0.4 mm (27 gauge), which are commonly used in eye surgery applications, although any other diameter may be used. The length of the exposed tube (i.e., the portion of cannula 100 extending from hub 104) could also be of any length, but preferably is between approximately 30 and 35 mm in length. Inner shaft 108 may be a corresponding smaller size which allows adequate flow for injection while allowing a sufficient gap for egress of fluid.

In terms of construction, outer shaft 102 may be made from stainless steel, but could also be made from plastics such as polyimide, nylon, PEEK or other similar materials. Inner shaft 108 can also be made from any of these same materials, though preferably from a material such as polyimide, which allows for the thinnest wall possible. The injection and egress ports can be cut in the side of outer shaft 102 using laser machining, electro discharge machining or any suitable method. The tube assembly can be bonded with instant adhesive or other means, depending on the tube material chosen.

The configuration of injection port 212 as a side port along cannula 100 eliminates the axial "jet" effect which can sometimes occur when in fluid is injected through an open end cannula (i.e., were lumen 210 to extend through tip 204). This "jet" effect can damage structures at the injection site, especially soft tissues such as the retina, by causing a perforation in the retina via the fluid stream and its impingement pressure. The untintentional transretinal injection of fluid can result in damage to the retina itself, a perforation, as well as fluid being unintentionally injected under the retina which may cause mechanical damage to structures beneath the retina such as Bruch's membrane, the retinal pigment epithelium, and the choroid. Further damage can occur when fluids intended to briefly contact the surface of the retina are deposited beneath the retina by inadvertent trans retinal injection due to chemical toxicity effects. Examples of this include subretinal heavy liquids such as perfluorocarbons or subretinal indocyanine green dye. Elimination of the axial "jet" effect therefore allows safer injection of fluids in these cases, especially near soft tissues such as the retinal surface.

In addition to injection port 212, cannula 100 may include any number of egress ports 214 also located along the circumference of outer shaft 102. In some embodiments, a bushing 208 or similar structure is located between inner shaft 108 and outer shaft 102 to fluidically isolate injection port 212 from the egress ports 214. In one embodiment, bushing 208 may be located approximately 1 millimeter from tip 204. During operation, bushing 208 acts as a seal to prevent fluid from entering the gap between outer shaft 102 and inner shaft 108 within tip portion 110 of cannula 100. Thus, fluid injected via inner shaft 108 and through injection port 212 may be prevented from flowing back into outer shaft 102 in the opposite direction towards egress port 214.

Egress ports 214 are generally configured to relieve fluid pressure from the injection site when a fluid is injected via injection port 212. For example, if the distal-most egress port 214 shown in FIG. 2 is also inserted into the injection site, fluid present at the injection site may be forced from the injection site through the egress port and back into lumen 210. Consequently, fluid pressure present at the injection site is relieved by providing a release channel 206 formed within lumen 210 for excess fluid to escape the injection site. In other words, egress ports 214 operate in conjunction to provide an egress for excess fluid at the injection site.

Figure 3:
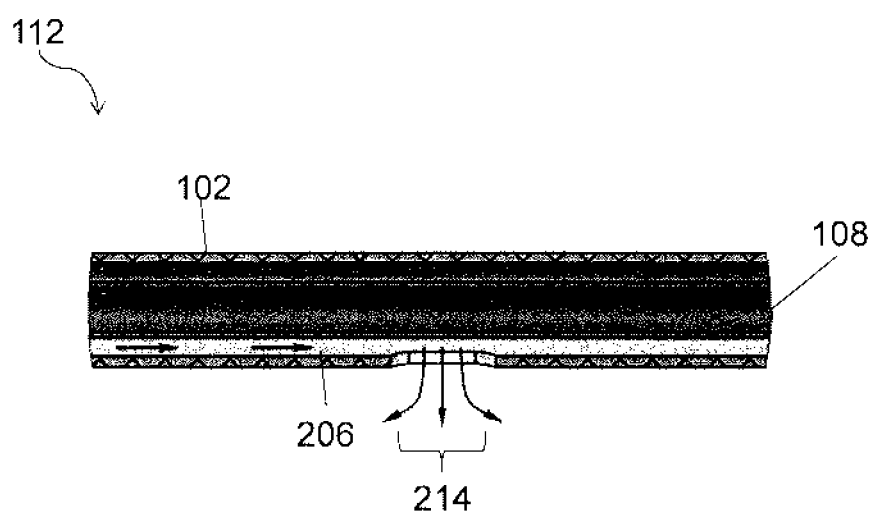
FIG. 3 is a cross-sectional view of a middle portion of the cannula of FIG. 1 shown in greater detail.

A cross-sectional view of middle portion 112 of cannula 100 is shown in greater detail in FIG. 3. As noted above, channel 206 formed between inner shaft 108 and outer shaft 102 provides a release channel for excess fluid from the injection site, thereby relieving fluid pressure from the site. When the excess fluid traveling through channel 206 reaches an egress port 214 that is not inserted into the injection site, the relieved fluid exits that egress port. In other words, channel 206 may provide a conduit whereby excess fluid at the injection site enters cannula 100 through any number of inserted egress ports 214 and is routed through any number of non-inserted egress ports 214 away from the injection site.

Figure 4:
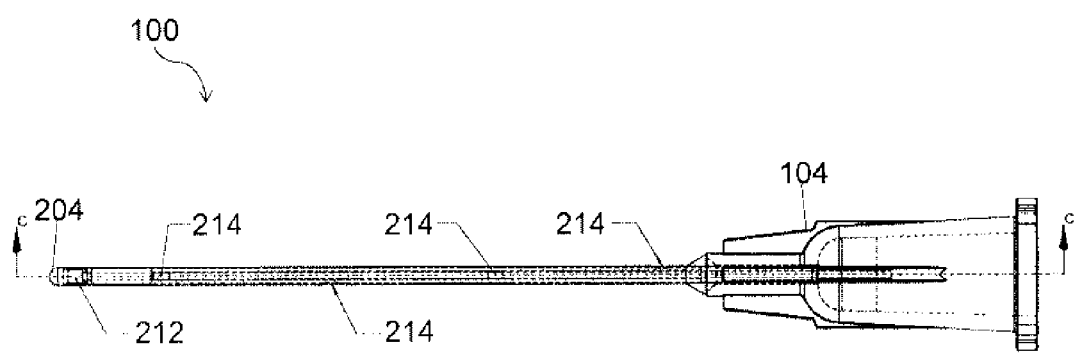
FIG. 4 is an example illustration of a dual lumen cannula having a plurality of egress ports.

Referring now to FIG. 4, an example illustration is shown of cannula 100 having a plurality of egress ports 214. The most proximal hole (i.e., one of egress ports 214) is located as near as practicable to hub 104 or other connection fitting. The distal-most hole (i.e., injection port 212) is located as near as practicable to the closed end of outer shaft 102 (i.e., tip 204). In between the distal and proximal holes are a series of openings in the tube (i.e., egress ports 214) and can vary in number from at least two to virtually any number, according to various embodiments. Injection port 212 and egress ports 214 may be a series of holes, elongated slots, micro holes, perforations, other variations, or combinations thereof. In various embodiments, injection port 212 and egress ports 214 may be arranged in a straight line or may be staggered around the circumference of outer shaft 102 in such a manner as to maximize the strength of the tube. In other words, injection port 212 and one or more of egress ports 214 may be located along a same line that runs parallel to the lumens of cannula 100. Alternatively, or in combination thereof, one or more of egress ports 214 is located at a different radial angle relative to the circumference of outer shaft 102 than that of injection port 212.

Advantageously, the plurality of egress ports 214 along outer shaft 102 allows a substantial increase in outflow capability over a similar device that may use only a single vent hole for fluid egress. This allows for faster pressure relief than currently available devices, enabling faster and easier injections with reduced overall intraocular pressure during injection.

In a non-limiting example of operation, cannula 100 may be attached to a syringe or similar apparatus, to enable injection of fluid into an eye during surgery. For example, cannula 100 may be inserted into an eye that has already been filled with a fluid such as BSS. At least one of the proximal egress ports 214 in outer shaft 102 remain outside of the eyeball. A fluid is injected inside the eyeball using the syringe or similar device, with the fluid exiting the device through injection port 212, which is the distal-most side port of cannula 100. As the pressure inside the eye increases, the fluid already in the eye is displaced and will passively egress through any of the distal egress ports 214 located proximally of the distal-most opening, which are located within the eyeball. The fluid will then egress through the gap between the inner and outer shafts 108, 102 (i.e., along channel 206) until it reaches the first proximal egress port 214 in outer shaft 102 located outside of the eye. The fluid will continue to passively displace through the egress port 214 until the pressure inside the eye is equalized with the pressure outside the eye. As the eye is filled with fluid as desired by the surgeon, cannula 100 may be slowly withdrawn. As cannula 100 is withdrawn from the eye, additional proximal egress ports 214 are exposed to the outside of the eye and fluid will egress through these ports. Cannula 100 therefore allows injection of fluid with simultaneous pressure release via egress of fluid through a secondary lumen, thereby enabling injection without an unsafe rise in intraocular pressure.

Preliminary tests conducted by three surgeons using a prototype of cannula 100 have proven to be highly favorable. In particular, 25 and 27 gauge cannulas according to the teachings herein were used in multiple retina surgical cases to inject perfluorocarbon liquid or staining dye. All three clinicians reported excellent results and a strong preference over existing cannula designs. The clinicians believed that the closed end design of cannula 100 eliminated the risk of perforating a retina with a "jet stream" of fluid. The clinicians also believed that the higher egress capacity of cannula 100 made the injection process faster without elevating intraocular pressure.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A cannula comprising:
    an outer shaft that defines a first lumen that only partially extends through the outer shaft and terminates at an injection port located along the circumference of the outer shaft; and
    an inner shaft located within the first lumen that defines a second lumen configured to convey fluid through the inner shaft and the injection port of the outer shaft into an injection site;
    wherein the outer shaft defines a plurality of egress ports located along the circumference of the outer shaft that are fluidically isolated from the injection port and configured to relieve fluid pressure from the injection site when fluid is conveyed from the second lumen into the injection site, and
    wherein at least one of the egress ports is extraneous to a cavity into which the fluid is injected.

2. The cannula of claim 1, further comprising:
    a bushing located between the outer and inner shafts and configured to fluidically isolate the injection port from the plurality of egress ports.

3. The cannula of claim 2, wherein the bushing is located within the first lumen approximately one millimeter from a tip of the inner shaft.

4. The cannula of claim 1, wherein a diameter of the outer shaft is between approximately 0.4 millimeters and 0.9 millimeters.

5. The cannula of claim 1, wherein the outer shaft comprises stainless steel.

6. The cannula of claim 1, wherein the outer shaft comprises a plastic material.

7. The cannula of claim 6, wherein the plastic material is selected from the group comprising nylon, polyimide, polyamide, and polyether ether ketone (PEEK).

8. The cannula of claim 1, wherein the injection port and at least one of the plurality of egress ports are located along a line that extends parallel to the first lumen.

9. The cannula of claim 8, wherein the injection port and the plurality of egress ports are located along the line.

10. The cannula of claim 1, wherein at least one of the plurality of egress ports is located at a different radial angle relative to the circumference of the outer shaft than that of the injection port.

11. The cannula of claim 1, further comprising:
    a syringe portion coupled to the inner shaft and configured to store the fluid.

12. The cannula of claim 11, wherein the outer shaft extends between approximately 30 and 35 millimeters from the syringe portion.

13. The cannula of claim 11, wherein a hub portion comprises a filler material.

14. A method comprising:
    conveying a fluid through a first lumen defined by an inner shaft of a cannula;
    conveying the fluid through an injection port located along a circumference of an outer shaft of the cannula and into an injection site, wherein the outer shaft of the cannula defines a second lumen configured to house the inner shaft; and
    conveying, in response to a fluid pressure at the injection site, fluid from the injection site through a plurality of egress ports located along the circumference of the outer shaft of the cannula that are fluidically isolated from the injection port,
    wherein at least one of the egress ports is extraneous to a cavity into which the fluid is injected.

15. The method of claim 14, further comprising:
    using a bushing to fluidically isolate the plurality of egress ports from the injection port.

16. The method of claim 14, further comprising:
    conveying the fluid from the injection site through an egress port located along a line that extends parallel to the first lumen and includes the injection port.

17. The method of claim 14, further comprising:
    conveying the fluid from the injection site through an egress port located along a line that extends parallel to the first lumen and includes the injection port.

18. The method of claim 14, further comprising:
    conveying the fluid from the injection site through an egress port located at a different radial angle relative to the circumference of the outer shaft than that of the injection port.

* * * * *